United States Patent
Meyer et al.

[11] Patent Number: 5,897,583
[45] Date of Patent: Apr. 27, 1999

[54] FLEXIBLE ARTIFICIAL NERVE PLATES

[75] Inventors: Jörg-Uwe Meyer, St. Ingbert; Thomas Stieglitz, Pirmasens, both of Germany

[73] Assignee: Fraunhofer Gesellschaft zur Forderung der Angewandten Forschung e.V., Germany

[21] Appl. No.: 08/765,742
[22] PCT Filed: Jul. 13, 1995
[86] PCT No.: PCT/EP95/02754
§ 371 Date: Mar. 18, 1997
§ 102(e) Date: Mar. 18, 1997
[87] PCT Pub. No.: WO96/02298
PCT Pub. Date: Feb. 1, 1996

[30] Foreign Application Priority Data

Jul. 13, 1994 [DE] Germany .............................. 44 24 697

[51] Int. Cl.$^6$ ..................................................... A61N 1/05
[52] U.S. Cl. .......................................................... 607/116
[58] Field of Search ................................. 607/50, 51, 115, 607/116, 118

[56] References Cited

U.S. PATENT DOCUMENTS 3,654,933  4/1972  Hagfors .
3,738,368  6/1973  Avery et al. .
3,774,618  11/1973  Avery .

*Primary Examiner*—Scott M. Getzow
*Attorney, Agent, or Firm*—Evenson, McKeown, Edwards & Lenahan, P.L.L.C.

[57] ABSTRACT

A flexible and non-conductive, artificial, implantable nerve plate has an E-module of about 3000–1000 N/mm$^2$ and a thickness of <50 μm for placement and insertion between the fascicles of a nerve bundle. Multiple electrodes are arranged on the two sides of the nerve plate, which is connected via conducting lines inside the nerve plate to a cable integrated with the nerve plate; and the cable is connectable to a control and signal receiver unit.

18 Claims, 1 Drawing Sheet

FLEXIBLE ARTIFICIAL NERVE PLATES

BACKGROUND AND SUMMARY OF THE INVENTION

The present invention relates to a flexible and nonconductive, artificial, implantable nerve plate ("flexible nerve plate", or FNP) for placement or insertion between the fascicles of a nerve bundle.

In the field of neuroprosthetics, new possibilities are being sought to contact nerve bundles and nerve fibers as gently as possible to a multiplicity of electrodes in order to derive multilocal and simultaneous nerve signals and/or stimulate nerve fibers. In this manner, by utilization of technical aid systems, it should also be possible to restore failed bodily functions by registering nerve signals and by stimulating nerves in the peripheral nerve system.

Interfascicular derivation techniques are used to detect nerve signals within a fascicle. (A fascicle is an organizational unit of nerve fibers within a nerve bundle.) Interfascicular electrodes are single bipolar electrodes, which derive both the electrical potential in the nerve fascicle and the electric potential at the nerve surface thereby making a differential measurement possible, which largely eliminates the disturbances caused by electromagnetic interferences. The signals from the sensory touch nerves of the front paws of cats were recorded with implanted interfascicular electrodes. Furthermore, motor nerves were successfully stimulated by means of implanted interfascicular electrodes.

The time and work consumed for precise placement of the electrodes, however, is considerable. As wire electrodes, the electrodes are single channel. Although new multi-channel silicon embodiments are in development, neither single nor multi-channel embodiments are sufficiently suited for permanent implantation. Moreover, the perineurium (the membrane around the fascicles) is damaged when the electrodes are inserted.

Shaft electrodes especially developed for the needs of an intracortical implantation, i.e. an implantation penetrating the pachymenix of the cerebral cortex or transmural, intracardial implantation, are known from IEEE Transactions on Biomedical Engineering vol. 39, No. 3, 1992, p. 271–279 and No. 5, p. 474–481. Insertion of a 125 μm thick Kapton foil between the fascicles in peripheral nerves is inconceivable, however, because the nerve is so badly degenerated, due to movement of the electrode as a consequence of muscle movement as well as due to the weight load and the momentary load on the nerve from the microelectrode as a result of gravity, that a derivation and simulation is not possible.

Kovacs has already demonstrated single-fiber contacting of proximal nerve stumps branching into meshlike microstructures. In order to aid the branching of the nerve stumps, a resection (removal of the fibrous-altered nerve section by cutting with a scalpel) must be conducted on the proximal stumps. This surgery does not seem suited for contacting large peripheral nerves (e.g. ischaeticus, n. femoralis) or for nerves without a total loss of continuity of function. Mesh electrodes are not suited for contacting healthy nerves, because free nerve endings are needed for branching through the mesh.

Since the 1970s, attempts have been made to stimulate and record neurograms with extraneural cuff-like electrodes, so-called cuff electrodes, which are placed encircling the nerve. Cuff electrodes have meanwhile become the most successful form of construction of biomedical electrodes and have found use in many fields. There are several U.S. patents for various forms of construction: for example, U.S. Pat. Nos. 3,774,618; 3,738,368; and 3,654,933. Some electrodes have been safely in use for 15 years. The number of electrodes is limited to three or four. Only a limited local resolution of the stimulation within the nerve can be achieved (tripolar electrodes). Drawback: multilocal stimulation (with more than four electrodes) of the nerve is only possible to a limited extent. Deeper structures can be achieved only with an increased stimulation current. Simultaneous stimulation and derivation is not possible.

One object of the present invention is therefore to permit simultaneous stimulation of the nerve and derivation of the nerve signal by means of an implant.

This object is achieved in accordance with the present invention, by means of a double-sided electrode arrangement and an interfascicular (between the fascicles) implantation, which permits successful direct multi-contacting of fascicles. An illustration of this advantage requires embarking on a brief explanation of neurophysiology.

A fascicle is a bundle of fibers, which is surrounded by the so-called perineurium, a type of enclosing layer, which compared to the epineurium (which gathers the fascicles, literally, to a nerve), is harder and also represents a protective layer for the nerve fibers. The concept of implanting nerve plates provides for implantation between the fascicles, so that the perineurium remains undamaged; therefore, less traumatization of the nerve or the nerve fibers is to be expected than with electrode concepts, in which the shaft electrodes are stuck into the nerve or the fascicle, thereby fundamentally risking injury to the perineurium. These fascicles are disposed functionally in the distal parts of the peripheral nerves, i.e. specific nerve fiber bundles are allocated to specific organs or parts of the body. Proximally peripheral and proximally central, this separation is frequently not clear. Due to the nerve plate concept, functional parts of the body or organs can be intentionally acted upon via the fascicles. By implanting of a flat, flexible structure in the nerve (and not around the nerve as in the case of cuff electrodes), deeper structures can be stimulated with small currents in such a manner that functional damage to the nerve from high currents due to the construction concept can be ruled out. Furthermore, damage to the nerve from pressure from post-operative aedema, as can occur with cuff electrodes, are avoided by means of this principle of construction at the peripheral nerve.

The double-sided arrangement of the electrodes permits simultaneous stimulation (on the one side of the plate) and derivation of the nerve signals (on the other side of the plate). If multiple electroneurograms are derived, the signal can be temporally-spatially resolved. By means of the many electrodes on both sides, stimulation and derivation of the nerve signals can also occur simultaneously on both sides with respective spacing of the electrodes or electrode blocks (FIG. 1), thereby improving the ability to detect or contact many nerve ends.

Hitherto attempts with electrodes, such as described above, have always used only one-sided electrodes, because in classical silicon technology, thinning wafers is conducted using a selective, wet chemical etching process in which the structure of the electrodes at the beginning of the process have to be defined by a diffusion of boron into the silicon substrate. Following this diffusion step, it is impossible to deposit or insert electrodes deeper into the substrate on the bottom diffusion front. After etching the samples free by means of EDP, it is also no longer possible, using semiconductor technology and micromechanics, to apply and to structure metal using thin film technology, to provide it with an insulating covering layer and then to open electrode windows. Giving up silicon in favor of polymer materials (polyimide) and the development of a process of double-sided placement of electrodes on a flat structure using multilayer technology, therefore, is a great improvement over the state of the art.

With the implanted, flexible nerve plate according to the invention, multi-local and simultaneous nerve signals can be permanently derived along multiple fascicles or nerve fibers, and nerves can be stimulated with little stimulation and without severing the nerve or traumatizing it permanently. This is the prerequisite for a multifunctional neuroprosthesis.

The FNP measures the cumulative action impulses in the interfascicular region and can only stimulate there. Single fiber contacting is not possible and not intended. The advantage of the present invention is the minimal traumatization with this implantation.

Procedures that were originally developed for cuff electrodes can be employed for electrode configuration and the design of the stimulation log. Using tripolar electrodes with control currents permits limiting the field to the immediate surroundings of the electrodes so that small fiber groups are stimulated. Differentiated stimulation logs using subtle prepulses also permits selectively stimulating more distant fascicles from the nerve plate. The nerve fibers can be excited according to their size by using block techniques (e.g. anodic block) or in the event of simultaneous stimulation by multiple adjacent electrodes.

Improvement and Advantages Over the State of the Art

Direct multiple contacting of fascicles and nerve fibers within a nerve bundle.

Simultaneous stimulation (e.g. of one side of the plate) and derivation (on the other side of the plate) is possible.

Multiple electrodes are located on a flat, flexible substrate, resulting in minimal traumatization of the nerve.

Mechanical stability by embedding the flexible nerve plate within the nerve fiber.

High temporal-spatial signal resolution.

The concept of the flexible nerve plate also represents a new approach in the technology of fabricating electrodes. In the microelectrodes hitherto fabricated using state of the art silicon technology, there is a clear separation of the substrate (mechanical stability), Metallization (electrodes and feed lines) and isolation layers and passivation layers (biocompatability, isolation of strip conductors). By means of the selection of a flexible, isolating material, such as polyimide, the prepared layers above and below the electrode metallization are used simultaneously for isolation and granting mechanical stability.

The flexible nerve plate is composed of a polymer and connection conducting lines inside the polymer or the polymer layers; that is, polyimide or silicon under slight tension, on both sides of which metal microelectrodes (e.g. platinum, iridium) are located. The microelectrodes can be printed on or vapor deposited. Along the longitudinal axis of the nerve plate there are 20–30 rows of electrodes, which may be of any desired configuration in order to be able to utilize the same FNP in principle both for derivation of electroneurograms and for stimulation. Strip conductors lead from the microelectrodes inside the nerve plate to a flexible, multi-layer band conductor (cable) integrated in the nerve plate. Signal-preprocessing microchips can be located on this multi-layer band conductor as can amplifiers or also antennas for an inductive coupling. In view of the fact that with polyimide the mentioned components cannot be monolithically integrated, a hybrid construction, e.g., the state of the art electronic components have to be constructed to form a circuit. These components having the respective miniaturized circuit can be disposed on the band conductor itself. The integrated construction of the band conductor with the nerve plate can eliminate a major source of errors: parting of the cable at the point of connection.

On the other hand, the band conductor can also be led through the skin and the control and signal receiver unit can be carried outside the body. If these components are also implanted on the band conductor, energy and signals can be transmitted in both directions (into and out of the body) by means of inductive coupling. An energy carrier, e.g. durable batteries, can also be implanted along with the nerve plate. In this case too, transmission of the signals occurs to electronics, in particular for evaluating the electroneurograms, which are disposed outside the body.

If the aim is essentially to stimulate and only a limited processing of the receiver electroneurograms is required, e.g. in electrotherapy, the electronic processing can also be carried out directly in the signal receiver unit provided on the band conductor.

Furthermore, an element of the present invention is that the implant is fabricated using multilayer technology.

In an especially advantageous process of fabrication, a silicon wafer or another carrier is employed essentially as a "processing aid" on which all the process steps occur. Alternately, a thin (2–20 µm) polyimide layer composed of a fluid prefabricated product is spun on and hardened by baking, and a metal layer is deposited and structured using thin film technology. The final layer is another polyimide layer. The polyimide of the created multilayer buildup is finally structured using a dry etching process (reactive ion etching:RIE). When fabricating numerous nerve plates on a single carrier, singling the nerve plates also occurs by means of RIE, making any desired shape of the exterior form (of the nerve plate) possible with greater precision, including the long, integrated cable to each nerve plate. At the end of the multilayer-nerve plate process, the nerve plates with the respective integrated cable can be detached from the silicon wafer. Their thickness is then approximately 10–30 µm.

Other objects, advantages and novel features of the present invention will become apparent from the following detailed description of the invention when considered in conjunction with the accompanying drawings.

DETAILED DESCRIPTION OF THE DRAWINGS

Figure 1:
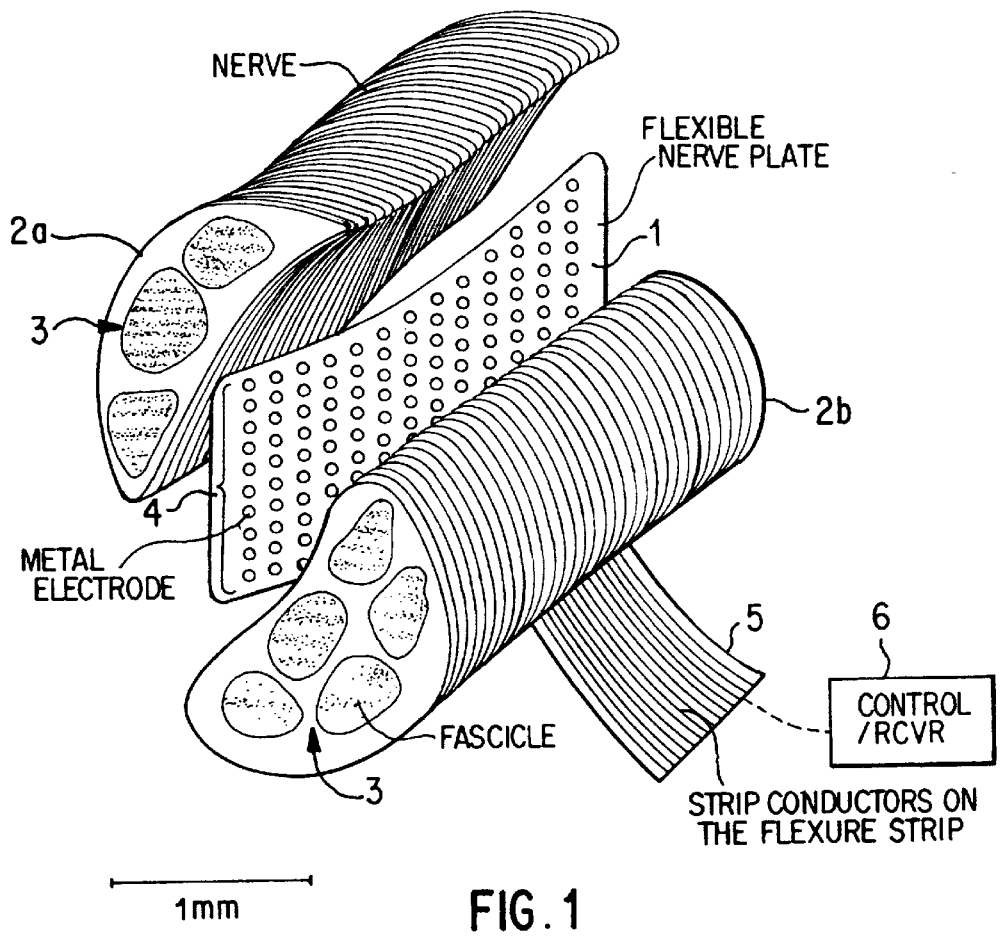
FIG. 1 is a perspective view of the flexible nerve plate according to the invention.

FIG. 1 shows an exploded three-dimensional perspective view of the nerve plate 1 according to the invention and a segment of the adjacent nerves 2a, 2b. The fascicles 3 can be seen at the ends of the nerve segments 2a, 2b, which are viewed in cross section. 5–30 rows of 2–20 electrodes 4 each, whose shape and position may be of any configuration, are deposited along the longitudinal axis of the nerve plate 1. Preferably, 20–300 electrodes are provided on each side of the nerve plate and can be controlled in a transmitting mode separately in any combination, or can be switched to a reception mode.

Figure 2:
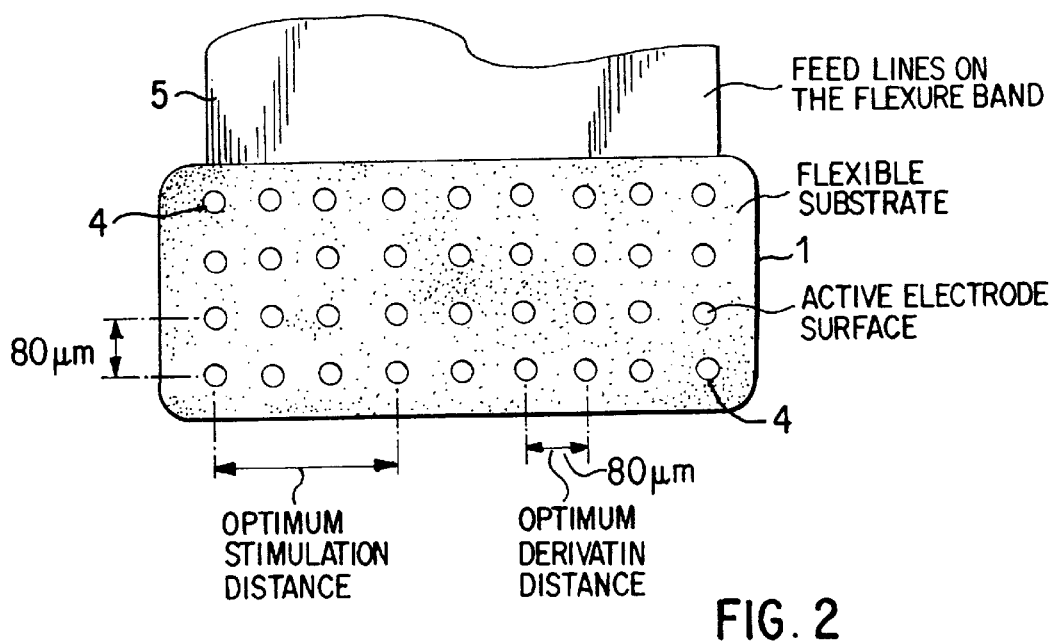
FIG. 2 is a plan view of the nerve plate of FIG. 1.

The spacing of the electrodes is, in the case of the electrodes for stimulation, preferably 150–250 µm and in the case of the electrodes for signal derivation, 80–120 µm as best seen in FIG. 2, which is a plan view of the nerve plate 1 of FIG. 1. Therefore, the same flexible nerve plate can fundamentally be utilized for derivation of electroneurograms (ENG) and for stimulation. (For this purpose the time for reception of signals may be from 2 to 100 times longer than the time for transmission.) The dimensions of the flexible nerve plate itself are approximately 2 mm×12 mm plus 10–50 mm for the cable 5.

The cable, or the flexible band conductor 5, is connected to the strip conductors inside the nerve plate 1 and therewith to the electrodes 4. At its distal end, the cable is connectable to a control and signal receiver unit 6 so that the electrodes can be intermittently stimulated by signals from the control unit, and can receive electro-neurograms.

During fabrication both types of strip conductors are simultaneously deposited, according to the state of the art, on the bottom polymer layer, e.g., vapor deposited. The electrodes and the strip conductors located inside the nerve plate are also deposited in one step, with the electrode layers being of thicker design. (The electrodes may also be concentrically surrounded by another electrode in which case, e.g., the inner electrode can be designed as a transmission electrode and the outer electrode as a receiver electrode, and each is connected to the respective signal processing unit.) Following this, the electrodes and conducting lines are then covered with another polymer layer and then the windows to the electrodes are produced.

The flexible nerve plate is placed between the fascicles of the nerve bundle, glued or sewn. With about 2–10 fascicles per nerve bundle and multiple utilized flexible nerve plates yield in this manner substantially more sites at which approximately 50,000 nerve fibers (approximately 5–7000 fibers per fascicle) can be excited or stimulated, or tapped (compared to the state of the art).

In another preferred embodiment, an intermediate layer composed of polymer material and thereupon a second metal layer are deposited on a bottom metal layer for the electrodes in such manner that to each side of the nerve plate belongs a whole "plane" of strip conductors. In this way, the strip conductors can be isolated better and more simply to the electrodes. The strip conductors are structured by means of a known lift-off process (e.g., singly), after which the respective electrode is located. After depositing the covering polymer layer, the windows to the electrodes are opened by means of the dry etching process. This can also be conducted for both sides of the nerve plates, likewise for the three-layer nerve plate.

The windows should be designed smaller than the electrode area so that the electrodes are anchored better in the nerve plate sandwich.

Further Preferred Embodiments

When employing functional electro-stimulation, e.g., via peripheral electrodes with paraplegics, it must be taken into account that paraplegia, which involves a loss of the inhibiting influence of dominant information relayed from the central nervous system, always is accompanied by various degrees of spasms. Before any motor simulation is useful or possible, the spasms must be released. Moreover, the contractions and the resulting pain, in addition to the paralysis and spasms, further diminish the patient's quality of life.

A possible way of reducing the spasms is electrotherapy. In this case, FNP can be employed, because the combination of electrodes permits the same large area of stimulation of whole groups of muscles. The implanted electrodes could substantially simplify the therapy and it could find greater acceptance by the patients and gain wider use. Therefore, FNP could be applied and used more widely before coding and decoding concepts have matured within the scope of "motoric neutrology" technology.

Another Preferred Embodiment

FNP could also be employed as an auditory brainstem implant. It offers a greater number of electrodes and good adaption to the surface of the nucleaus cochlearis. In order for the FNP to remain at the desired location, the substrate can be designed as a sieve structure, in such a manner that fibroblasts growing through the sieve attach it. Stimulation with greater spatial resolution permits improved imaging of the ambient noises, which may lie in the direction of actual speech recognition.

As an implant in the visual cortex, FNP records a middle way between epidural, i.e. lying on the dura mater, and intracortical solutions of electrode configurations. It can be placed in the arachoid region and, due to its flexibility, adapt to the windings of the visual cortex (V1 area 17) in the occipital lobes. It is conceivable that placing one FNP in each of the sulcus calcarinus of both halves of the brain respectively, which is covered by the sclera. In this configuration, the stimulating electrodes are separated only by the soft pia mater from the nerve areas to be stimulated, however, without directly penetrating and damaging the sensitive tissue of the meninx. There is a functional division of the sclera into columns with approximately 300–500 µm diameter that run perpendicular to the surface through the whole width of the cortex. They belong to the circumscribed regions of the retina and are visuo-optically allocated. By surface stimulation of the perpendicular columns, which are allocated to the circumscribed regions of the retina, generation of phosphenes is expected which due to the electrode density and combination made possible by FNP permits perception of different shapes.

Although the invention has been described and illustrated in detail, it is to be clearly understood that the same is by way of illustration and example, and is not to be taken by way of limitation. The spirit and scope of the present invention are to be limited only by the terms of the appended claims.

What is claimed is:

1. An arrangement for electrically contacting nerve bundles and nerve fibers, comprising:

a flexible, non-conductive, implantable nerve plate for insertion between fascicles of a nerve bundle, said nerve plate have an E-module in a range of from 1,000 to 3,000 N/mm$^2$ and a thickness of less than 50 µm;

a plurality of electrodes arranged on opposite sides of said nerve plate; and a plurality of conducting lines arranged inside said nerve plate and connecting said electrodes to a cable which is integrated with said nerve plate, said cable being connectable to a control and signal receiver unit.

2. Arrangement according to claim 1 wherein said nerve plate comprises a polymer material.

3. Arrangement according to claim 2 wherein said polymer material is selected from the group consisting of polyimide and a silicone polymer material.

4. Arrangement according to claim 1 wherein said E-module is in a range of from 2,000 to 2,500 N/mm$^2$.

5. Arrangement according to claim 1 wherein said thickness is <20 µm.

6. Arrangement according to claim 1 wherein said thickness is <10 µm.

7. Arrangement according to claim 1 wherein said electrodes are made of a material selected from the group consisting of platinum, iridium, iridium oxide and gold; and said electrodes are connected to one of said control unit for stimulation of the nerves and said signal receiver unit for reception of electroneurograms.

8. Arrangement according to claim 7, wherein transmitter and receiver electrodes are disposed separately on said opposite sides or mixed on both of said opposite sides.

9. Arrangement according to claim 1, wherein said control and signal receiver unit is designed in such a manner that said electrodes can be intermittently impinged with signals for stimulation of the nerves and can receive electroneurograms.

10. Arrangement according to claim 9, wherein times for reception and transmission are of different length, said reception time being 2–100 times longer than the transmission times.

11. Arrangement according to claim 1, wherein 20–300 electrodes are provided on each side of the nerve plate, disposed in rows and columns, and can be controlled in a transmitting mode separately in any combination or can be switched to reception.

12. Arrangement according to claim 1, wherein said cable is designed as a flat strip cable, and is integrated in multiple layers with the nerve plate.

13. Arrangement according to claim 1, wherein said control and signal receiver unit has at least one of preamplifiers and amplifiers and devices of hybrid construction on or at said flat strip cable, for inductive coupling for said transmitter respectively said receiver outside the body.

14. A process for fabricating the flexible, artificial nerve plate of claim 13 for placement or insertion between the fascicles of a nerve bundle having multiple electrodes on one or both sides of said nerve plate having conducting lines inside said nerve plate, and an integrated cable, wherein said nerve plate is fabricated using multilayer technology.

15. A process according to claim 14, wherein said process comprises the steps of:

applying a polymer material by one of spinning, sputtering and spraying on a carrier;

hardening said polymer material by heating;

applying said electrodes and said conducting lines connected thereto inside said nerve plates and said cable, using thin film technology;

applying a second polymer layer;

hardening said second polymer layer;

removing said polymer layer on the electrodes; and removing the multilayer on said carrier.

16. A process according to claim 15, wherein multiple nerve plates having integrated cables are fabricated in various forms of construction on one silicon wafer.

17. A process according to claim 15, wherein said polymer layers are structured by means of dry etching processes, e.g., reactive ion etching, and, in particular, the electrodes being exposed, and if need be, multiple nerve plates being separated by means of said process.

18. A process according to claim 15, wherein two metal layers having a layer composed of said polymer material lying therebetween are fabricated in such a manner that said nerve plate comprises five layers.

* * * * *